(12) United States Patent
Mohamed Elmahdy et al.

(10) Patent No.: US 11,039,761 B2
(45) Date of Patent: Jun. 22, 2021

(54) FALL PREDICTION BASED ON ELECTROENCEPHALOGRAPHY AND GAIT ANALYSIS DATA

(71) Applicant: AT&T Intellectual Property I, L.P., Atlanta, GA (US)

(72) Inventors: Mohamed Ahmed Mohamed Elmahdy, Houston, TX (US); Shaoda Yu, Katy, TX (US); Nadia Morris, Houston, TX (US); David R. Eguren, Houston, TX (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 264 days.

(21) Appl. No.: 16/220,655

(22) Filed: Dec. 14, 2018

(65) Prior Publication Data

US 2020/0187829 A1 Jun. 18, 2020

(51) Int. Cl.
G08B 23/00 (2006.01)
A61B 5/11 (2006.01)
A61B 5/00 (2006.01)
A61B 5/291 (2021.01)

(52) U.S. Cl.
CPC ............ *A61B 5/112* (2013.01); *A61B 5/1117* (2013.01); *A61B 5/291* (2021.01); *A61B 5/6803* (2013.01); *A61B 5/6807* (2013.01); *A61B 5/7275* (2013.01); *A61B 5/746* (2013.01); *A61B 2562/0219* (2013.01); *A61B 2562/0247* (2013.01)

(58) Field of Classification Search
CPC ..... A61B 5/112; A61B 5/0478; A61B 5/1117; A61B 5/6803; A61B 5/6807; A61B 5/7275; A61B 5/746; A61B 2562/0219; A61B 2562/0247
USPC ..................................................... 340/573.1
See application file for complete search history.

(56) References Cited

U.S. PATENT DOCUMENTS

| | | | |
|---|---|---|---|
| 7,612,681 B2 | 11/2009 | Azzaro et al. | |
| 8,206,325 B1 * | 6/2012 | Najafi | A61B 5/1116 600/595 |
| 8,773,269 B2 * | 7/2014 | Richardson | G08B 21/0446 340/573.7 |
| 8,823,526 B2 | 9/2014 | Kaiser et al. | |
| 8,990,041 B2 | 3/2015 | Grabiner et al. | |
| 9,351,640 B2 | 5/2016 | Tran | |
| 9,607,498 B2 | 3/2017 | Osorio | |

(Continued)

*Primary Examiner* — Kerri L McNally
*Assistant Examiner* — Thang D Tran

(57) ABSTRACT

A method, a computer-readable storage device, and an apparatus for predicting a fall are disclosed. In one example, a method performed by a processor deployed in a communications network includes collecting gait information associated with a user from a first wearable device worn by the user, collecting electroencephalography information associated with the user from a second wearable device worn by the user, calculating a likelihood that the user will fall within a threshold period of time from a current time, wherein the calculating is based on a combination of the gait information and the electroencephalography information; and sending an instruction to an endpoint device associated with the user when the likelihood exceeds a predefined threshold, wherein the instruction instructs the endpoint device to generate an alert alerting the user that a fall is likely.

20 Claims, 3 Drawing Sheets

(56) References Cited

U.S. PATENT DOCUMENTS

| | | | |
|---|---|---|---|
| 9,640,057 B1 | 5/2017 | Ross | |
| 9,999,377 B2 | 6/2018 | Osorio | |
| 10,052,062 B2 | 8/2018 | De Sapio et al. | |
| 10,198,928 B1* | 2/2019 | Ross | A61B 5/7267 |
| 2006/0279426 A1* | 12/2006 | Bonnet | A61B 5/1117 |
| | | | 340/573.1 |
| 2008/0129518 A1* | 6/2008 | Carlton-Foss | G08B 25/10 |
| | | | 340/573.1 |
| 2008/0186189 A1* | 8/2008 | Azzaro | G16H 15/00 |
| | | | 340/573.7 |
| 2009/0216156 A1* | 8/2009 | Lengsfeld | A61B 5/1038 |
| | | | 600/595 |
| 2009/0260426 A1* | 10/2009 | Lieberman | A61B 5/1116 |
| | | | 73/65.01 |
| 2012/0092169 A1* | 4/2012 | Kaiser | A61B 5/6807 |
| | | | 340/573.1 |
| 2012/0095722 A1* | 4/2012 | Ten Kate | A61B 5/1117 |
| | | | 702/141 |
| 2012/0101411 A1* | 4/2012 | Hausdorff | A61B 5/6831 |
| | | | 600/595 |
| 2012/0101770 A1* | 4/2012 | Grabiner | G16H 50/20 |
| | | | 702/141 |
| 2012/0253234 A1* | 10/2012 | Yang | A61B 5/1038 |
| | | | 600/595 |
| 2013/0120147 A1* | 5/2013 | Narasimhan | A61B 5/1117 |
| | | | 340/573.1 |
| 2014/0245783 A1* | 9/2014 | Proud | G16H 40/67 |
| | | | 63/1.11 |
| 2014/0276238 A1* | 9/2014 | Osorio | A61B 5/1117 |
| | | | 600/595 |
| 2014/0276242 A1* | 9/2014 | Chen | A61B 5/1116 |
| | | | 600/595 |
| 2015/0092972 A1* | 4/2015 | Lai | H04R 1/1008 |
| | | | 381/333 |
| 2015/0112163 A1 | 4/2015 | Wilmink | |
| 2015/0196231 A1* | 7/2015 | Ziaie | A61B 5/1117 |
| | | | 600/595 |
| 2015/0260514 A1* | 9/2015 | Menelas | G01V 9/00 |
| | | | 702/2 |
| 2016/0007910 A1* | 1/2016 | Boss | A61B 5/6803 |
| | | | 600/301 |
| 2016/0120432 A1* | 5/2016 | Sridhar | A61B 5/4082 |
| | | | 600/544 |
| 2017/0000693 A1* | 1/2017 | Orr | A61J 7/0418 |
| 2017/0238812 A1* | 8/2017 | Atlas | A61B 5/1117 |
| 2017/0258410 A1* | 9/2017 | Gras | A61B 5/746 |
| 2017/0303849 A1* | 10/2017 | De Sapio | A61B 5/1117 |
| 2017/0325738 A1* | 11/2017 | Antos | A61B 5/6803 |
| 2017/0352240 A1* | 12/2017 | Carlton-Foss | A61B 5/1116 |
| 2017/0354341 A1* | 12/2017 | Kadambi | A61B 5/0476 |
| 2017/0358195 A1* | 12/2017 | Bobda | H04N 7/188 |
| 2018/0000385 A1* | 1/2018 | Heaton | G08B 29/186 |
| 2018/0064373 A1* | 3/2018 | Regev | A61B 8/488 |
| 2018/0153470 A1* | 6/2018 | Gunasekar | A61B 5/0478 |
| 2018/0177436 A1* | 6/2018 | Chang | A61B 5/112 |
| 2018/0228405 A1* | 8/2018 | Burwinkle | A61B 5/0002 |
| 2018/0233018 A1* | 8/2018 | Burwinkel | G08B 21/0492 |
| 2018/0279915 A1* | 10/2018 | Huang | A61B 5/7264 |
| 2018/0333083 A1 | 11/2018 | Orellano | |
| 2018/0357879 A1 | 12/2018 | Negre et al. | |

\* cited by examiner

FALL PREDICTION BASED ON ELECTROENCEPHALOGRAPHY AND GAIT ANALYSIS DATA

The present disclosure relates generally to healthcare, and relates more particularly to devices, computer-readable media, and methods for predicting falls based on a combination of electroencephalography data and gait analysis.

BACKGROUND

Falls pose serious hazards for older individuals as coordination, muscle strength, and balance tend to deteriorate with age and advance of chronic diseases such as Parkinson's disease and the like. In managed care as well as home settings, injuries resulting from falls may render older individuals incapable of calling for help and/or requiring emergency treatment. Resulting bone fractures can require lengthy and costly treatment, severely impact quality of life, and can trigger a cascade of other factors that lead to a rapid decline of the health of an individual.

SUMMARY

A method, a computer-readable storage device, and an apparatus for predicting a fall are disclosed. In one example, a method performed by a processor deployed in a communications network includes collecting gait information associated with a user from a first wearable device worn by the user, collecting electroencephalography information associated with the user from a second wearable device worn by the user, calculating a likelihood that the user will fall within a threshold period of time from a current time, wherein the calculating is based on a combination of the gait information and the electroencephalography information; and sending an instruction to an endpoint device associated with the user when the likelihood exceeds a predefined threshold, wherein the instruction instructs the endpoint device to generate an alert alerting the user that a fall is likely.

In another example, a computer-readable storage device stores instructions which, when executed by a processor deployed in a communication network, cause the processor to perform operations. The operations include collecting gait information associated with a user from a first wearable device worn by the user, collecting electroencephalography information associated with the user from a second wearable device worn by the user, calculating a likelihood that the user will fall within a threshold period of time from a current time, wherein the calculating is based on a combination of the gait information and the electroencephalography information; and sending an instruction to an endpoint device associated with the user when the likelihood exceeds a predefined threshold, wherein the instruction instructs the endpoint device to generate an alert alerting the user that a fall is likely.

In another example, an apparatus includes a processor deployed in a communication network and a computer-readable medium storing instructions which, when executed by a processor deployed in a communication network, cause the processor to perform operations. The operations include collecting gait information associated with a user from a first wearable device worn by the user, collecting electroencephalography information associated with the user from a second wearable device worn by the user, calculating a likelihood that the user will fall within a threshold period of time from a current time, wherein the calculating is based on a combination of the gait information and the electroencephalography information; and sending an instruction to an endpoint device associated with the user when the likelihood exceeds a predefined threshold, wherein the instruction instructs the endpoint device to generate an alert alerting the user that a fall is likely.

BRIEF DESCRIPTION OF THE DRAWINGS

The present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

The present disclosure relates generally to predicting falls based on a combination of electroencephalography (EEG) data and gait analysis. As discussed above, falls pose serious hazards for older individuals. Although technology (such as wearable monitors) has been developed to detect when falls occur, such technology can at best only limit the severity of an injury by ensuring that timely aid is provided. Since a fall must occur in order for the technology to react, a significant risk of injury still exists.

Examples of the present disclosure aim to predict the likelihood that an individual will fall before a fall actually occurs (e.g., in substantially real time), and therefore aim to prevent significant injury to the individual. In one example, a shoe insole having built-in force resisting sensors and a headband having built-in EEG sensors are used to monitor the individual's gait and brain electrical activity, respectively, for signs that the individual may be likely to fall. For instance, the insole and the headband may continuously stream information to a network-based monitoring server that performs gait and neurological analysis and calculates the likelihood of a fall.

Thus, examples of the disclosure leverage the fact that there is a strong link between cognition and changes in gait patterns (for instance, changes in gait can be used to detect early signs of cognitive aberrations). As an example, Alzheimer's disease primarily affects the hippocampus region of the brain (which is a key area of the brain for the formation of new memories) and may also manifest in changes in gait (e.g., cautious gait in the early stages and frontal gait disorders in the later stages). Parkinson's disease may affect the substantia nigra (which is a key area of the brain for dopamine synthesis) and may manifest in small, shuffling steps and reduced stride length and walking speed. Amyotrophic lateral sclerosis (ALS) typically affects the motor neurons and may manifest in excessive knee flexion at initial content and diminished plantarflexion at weight release.

Examples of the present disclosure may also be used to evaluate the efficacy of medication regimens in individuals with gait abnormalities. For instance, some medications have been shown to improve gait in elderly patients. In such a case, simultaneous analysis of EEG and gait data may allow healthcare providers (e.g., doctors, physical therapists, etc.) to track changes and progress in a patient's gait after beginning a new medication regimen.

Further examples of the present disclosure may be used to analyze the gait of an individual who uses a personal exoskeleton or similar device (e.g., to treat multiple sclerosis or cerebral palsy, recover from paralysis or stroke, or the like). For instance, examples of the present disclosure could be used to detect and correct characteristics of the individual's gait that may make falls likely.

Figure 1:
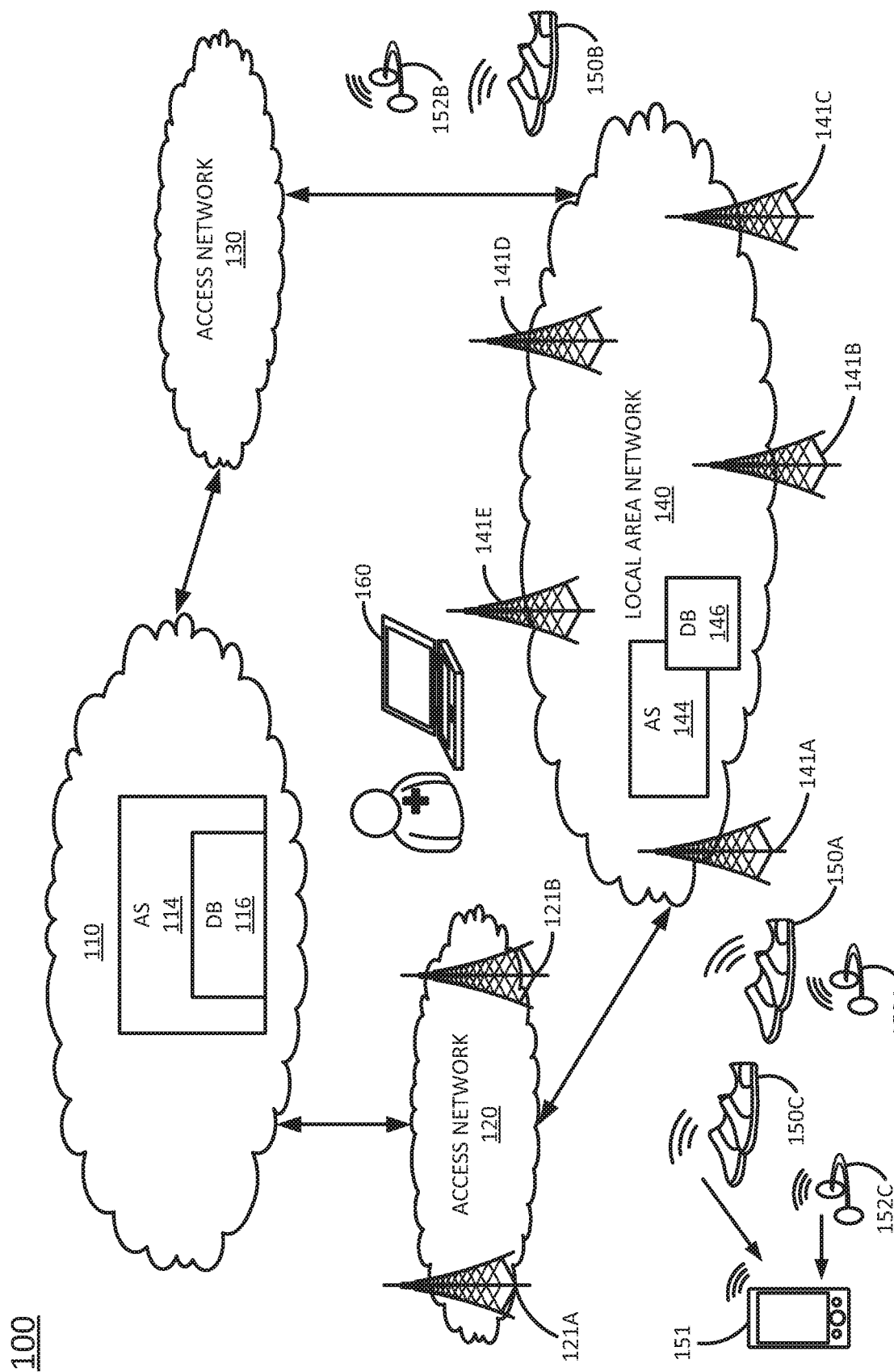
FIG. 1 illustrates one example of a communication network of the present disclosure.

To aid in understanding the present disclosure, FIG. 1 is a block diagram depicting one example of a communication network 100 suitable for use in performing or enabling some or all of the features described herein. The communication network 100 may be any type of communication network, such as for example, a traditional circuit switched network (e.g., a public switched telephone network (PSTN)) or a packet network such as an Internet Protocol (IP) network (e.g., an IP Multimedia Subsystem (IMS) network), an asynchronous transfer mode (ATM) network, a wireless network, a cellular network (e.g., 2G, 3G, 4G, and future generations), a long term evolution (LTE) network, and the like related to the current disclosure. It should be noted that an IP network is broadly defined as a network that uses Internet Protocol to exchange data packets.

In one example, the network 100 may comprise a core network 110. The core network 110 may be in communication with one or more access networks 120 and 130. For instance, access network 120 may comprise a wireless access network (e.g., an IEEE 802.11/Wi-Fi network, a wide area network (WAN) and the like) or a cellular access network. Thus, in one example, access network 120 may include one or more wireless transceivers 121A and 121B, which may alternatively comprise cellular base stations, base transceiver stations (BTSs), NodeBs, evolved NodeB's (eNodeBs), wireless access points, and so forth. Similarly, access network 130 may comprise a wired access network such as a circuit switched access network, a cable access network, a digital subscriber line (DSL) access network, and so forth. The core network 110 and the access networks 120 and 130 may be operated by different service providers, the same service provider or a combination thereof.

In one example, network 100 also includes a local area network (LAN) 140. For example, local area network 140 may comprise a wireless local area network (LAN), a Bluetooth network, a ZigBee network, and so forth. For instance, local area network 140 may be a home network or an office network, e.g., a network that is maintained by a hospital, an elder care facility, a rehabilitation center, and so forth. As illustrated, local area network 140 may comprise a coverage network or mesh network of ZigBee access points 141A-141E which may be connected to one another and to other devices and networks via an Ethernet network. However, it should be noted that ZigBee is designed for static end nodes. Thus, local area network 140 may comprise a ZigBee mesh network modified to enable handoffs between the different ZigBee access points 141A-141E.

In one example, the ZigBee access points 141A-141E are in communication with one or more wearable devices 150A-150C and 152A-152C. In one example, each of the wearable devices 150A-150O may comprise one or a pair of smart shoe insoles or inserts, while each of the wearable device 152A-152C may comprise a smart EEG headset. The term "smart" implies the ability to measure, record, process, and communicate information.

In one example, each of the smart shoe insoles 150A-150C may include one or more built-in components for collecting gait information of a user, such as force resisting sensors, accelerometers, and/or gyroscopes. In one example, a user may use a respective smart shoe insole for each foot (e.g., an insole in each shoe). However, in another example it may be sufficient to use a smart shoe insole 150A-150C for only one foot (e.g., an insole in one shoe).

In one example, each of the smart EEG headsets 152A-152C may comprise a headband, hat, or other head-mounted device that includes a plurality of built-in EEG sensors or electrodes. For instance, the EEG sensors may be grouped into one or more locations to contact different portions of a user's head, such as the forehead and behind each ear.

Notably, the users, and hence the wearable devices 150A-150O and 152A-152O, may move throughout the coverage area of local area network 140, thus benefiting from the ability of handing off between the ZigBee access points 141A-141E. The wearable devices 150A-150O and 152A-152C may also include notification means, such as an audio alarm, to warn a user of danger (e.g., unstable gait that could result in a proximate fall).

Figure 3:
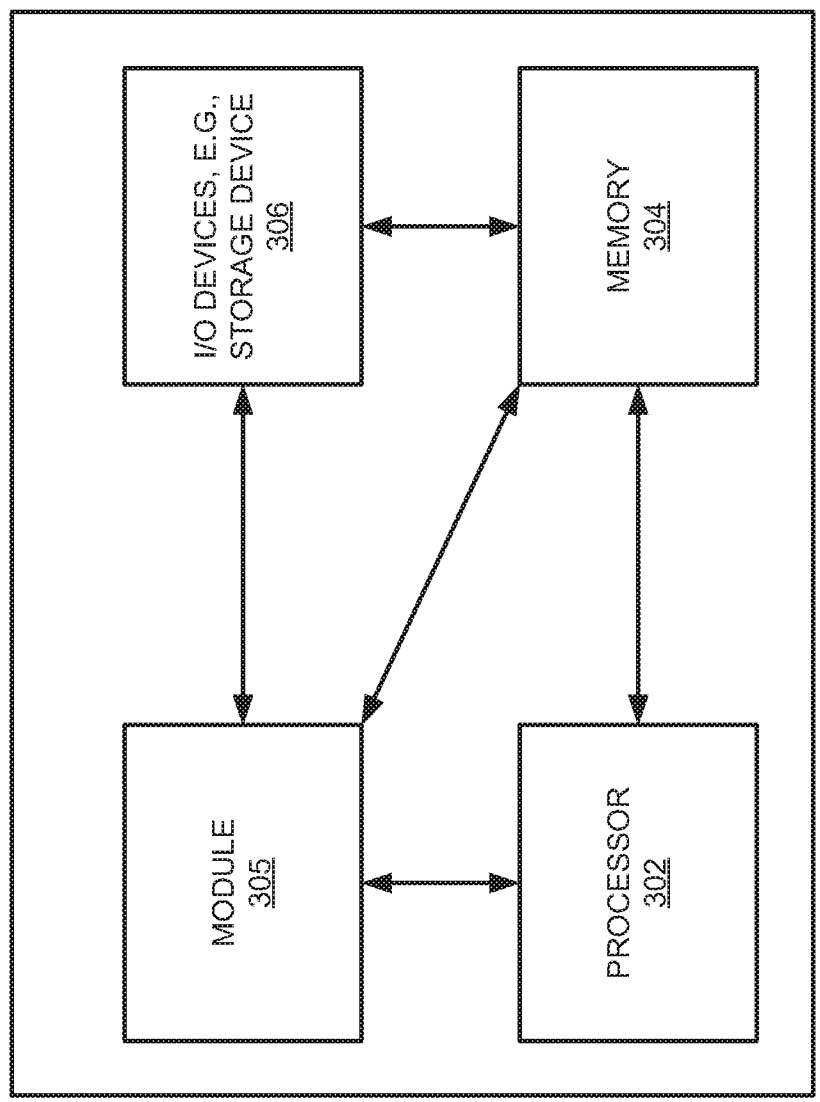
FIG. 3 illustrates a high-level block diagram of a general-purpose computer suitable for use in performing the functions described herein.

In one example, the core network 110 may include an application server (AS) 114 and a database (DB) 116. Notably, AS 114 may perform some or all of the functions described herein in connection with predicting falls. For example, AS 114 may collect and store in database 116 user gait information and EEG readings received from the wearable devices 150A-150O and 152A-152O. Database 116 may also store user profiles, generic signatures for different modes of motion or types of activities, disease/medical condition profiles, including signatures for different stages of one or more diseases, and so forth. In one example, gait information may be forwarded from local area network 140 via access network 120 and/or access network 130 to AS 114. At AS 114, the gait information may be collected, stored in database 116 and used for predicting a fall. In one example, the AS 114 may comprise a general purpose computer as illustrated in FIG. 3 and discussed below. Notably, AS 114 is suitable for performing some or all of the functions of the present disclosure for predicting falls as described in greater detail below. In addition, although only a single AS 114 and a single DB 116 are illustrated in core network 110, it should be noted that any number of application servers 114 or databases 116 may be deployed.

In one example, the gait information and EEG readings include information which identifies a particular wearable device or set of wearable devices as a source of the gait information or EEG readings. The gait information may also include pressure information, acceleration information (including both linear and rotational accelerations), gyroscopic information, elevation information, time information, and/or location information. In particular, raw gait information, such as pressure information, acceleration information, gyroscopic information, elevation information, temperature, and fluid content (edema) may be collected from the various sensors of a smart insole 150A-150C. The EEG information may also include acceleration information (including both linear and rotational accelerations), gyroscopic information, elevation information, time information, and/or location information.

Other components may also contribute to the gait information and EEG information prior to the gait information and EEG information reaching AS 114. For example, each of the ZigBee access points 141A-141E may time stamp any gait information or EEG information that is received from one of the wearable devices 150A-150O or 152A-152O. In addition, in one example the ZigBee access points 141A-141E may also append their location information to any gait information or EEG information that is received. In another example, each ZigBee access point 141A-141E may simply append its own identity to any gait information or EEG information that is received, where the identity information is sufficient to indicate the approximate location of the user relative to a corresponding ZigBee access point.

In one example, AS 114 may also determine characteristics of motion information from the gait information. For example, AS 114 may gather gait information relating to a user over a period of time, e.g., over an hour, over a day, over a week, and so forth. From the gait information, AS 114 may then determine characteristics of motion such as a stride length, a speed, an acceleration, an elevation, and so forth, as well as different modes of motion or different types of activities that a user has engaged in at various times within the time period. For example, accelerometers within one of the smart insoles 150A-150O may indicate accelerations along different axes. Accordingly, the raw gait information may simply include an acceleration and an indication of which component recorded the acceleration. Different accelerations may then be vector summed by AS 114 to derive an overall acceleration magnitude and direction which may then be included as part of the characteristics of motion information.

As another example, to determine a mode of motion for any particular time within the time period, AS 114 may compare the gait information and/or characteristics of motion information to known signatures for different common modes of motion that are stored in database 116. Exemplary modes of motion may broadly include postures, stances, movement patterns and/or types of activities such as: running, walking, falling, jumping, standing, cycling, sitting, shuffling, and lying down and so forth. It should be noted that "running" may optionally be further defined with more granularity such as speed walking, jogging, sprinting, and the like. For instance, a running signature may indicate a sequence of: a strong pressure on the left foot, acceleration of the right foot, a strong force and deceleration of the right foot, acceleration of the left foot, and so forth. On the other hand, a walking signature may be similar to the running signature, but the forces and accelerations observed may be of lesser magnitude than the signature for running. Similarly, a standing signature may comprise steady and balanced pressures on both feet (with zero acceleration).

In one example, AS 114 may also determine characteristics of neurological activity from the EEG information. For example, AS 114 may gather EEG information relating to a user over a period of time, e.g., over an hour, over a day, over a week, and so forth. From the EEG information, AS 114 may then determine characteristics of neurological activity such as a reaction to a stimulus, neural oscillations, eye blinks, and so forth.

Various characteristics of motion, such as speed and stride length, may be determined from gait information in various ways. For instance, in one example, global positioning system (GPS) location data is included in or appended to the gait information to allow a change in position over time to be determined. In this way, the average speed and speed at various times may be calculated. In addition, if the mode of motion is determined to be running or walking, the distance traveled in a particular time divided by a number of stances, e.g., steps, observed in the same time will indicate the average stride length. In another example, one or more of the smart insoles 150A-150O may include a pair of sensors, one for each foot, to determine a distance between the sensors. For example, the sensors can send and measure a round-trip time between the sensors, e.g., using infrared signals, radio frequency (RF) signals, acoustic signals, and the like to estimate a distance between the sensors.

In another example, GPS location data may be unavailable. Accordingly, the gait information and/or EEG information may include position information derived from one or more other sources. For instance, each of the ZigBee access points 141A-141E may append its identity and/or location information to any gait information and/or EEG information that the ZigBee access point receives and forwards, thereby allowing AS 114 to determine the approximate location of a user at different times. For example, at a first time, gait information for the smart insoles 150A may be received and appended with the identity and/or location of ZigBee access point 141A. At a later time, gait information may be received for the same smart insoles 150A from ZigBee access point 141B. Thus, AS 114 can determine the approximate distance travelled, speed and so forth, based upon the difference in positions of the respective ZigBee access points.

Once various characteristics of motion and electrical activity are determined, AS 114 may then determine whether or not a fall is likely in view of the gait information/characteristics of motion information and electrical activity. When AS 114 determines that the likelihood of a fall exceeds a predefined threshold, AS 114 may also transmit a notification to one or more parties. For example, AS 114 may notify the user, a doctor, a nurse, a physical therapist and so forth, when the determination is made. For example, AS 114 may transmit an instruction to one of the wearable devices 150A-150C and 152A-152C or to an endpoint device 151 or 160 of a user or doctor, where the instruction instructs the wearable device or the endpoint device to activate an alert (e.g., a visible, audible, and/or haptic alert). The alert to the user or other appropriate entities may encourage the user or other individuals in the user's vicinity (e.g., caregivers) to exercise increased caution (e.g., walk more slowly or take a break), to seek or offer physical assistance, or the like.

In one example, database 116 stores a user profile which stores biometric information regarding a user and which tracks a user over multiple time periods. For instance, the user profile may store the age, weight, height, metabolic rate and so forth for the user. The user profile may also store data regarding the prior activity levels of the user in terms of stride length, distances travelled, speed of walking, running, cycling, etc., calories burned, and so forth. The user profile may further store data regarding previous determinations of the user as being associated with a particular disease and/or disease stage which may affect gait.

In some cases, it may be helpful to know beforehand that a user has been diagnosed with a particular medical condition/disease, as certain conditions or diseases may be associated with a heightened risk of falling (e.g., Parkinson's disease, muscular dystrophy, multiple sclerosis, Alzheimer disease, Huntington disease, adrenoleukodystrophy, ataxia, dystonia, multiple system atrophy, arthritis (including osteoarthritis and rheumatoid arthritis), dementia, and similar diseases and/or conditions that are associated with altered gait). Thus, in one example, database 116 may store different medical condition profiles, each profile including various signatures associated with different stages of one of several medical conditions. Accordingly, AS 114 may match observed or expected gait information/characteristics of motion information to the best-fit signature.

The foregoing describes various functions of AS 114 (and database 116) in connection with examples of the present disclosure for predicting falls. However, it should be noted that in one example, local area network 140 may also include an application server (AS) 144 and a database 146 which may perform the same or similar functions to those of AS 114 in core network 110. In other words, AS 144 may also collect and store user gait information and EEG information from the one or more wearable devices 150A-150O and 152A-152O via the ZigBee access points 141A-141E. Database 146 may also store user profiles, instructions relating to the tracking of different users, mode of motion signatures, disease profiles, and so forth to allow AS 144 to determine characteristics of motion information and/or to predict a likelihood of a fall. In one example local area network 140 also provides access for endpoint device 160, e.g., a personal computer, a laptop computer, tablet computer, smart phone, and the like to connect to AS 144 and/or AS 114. For example, a doctor, a nurse, a technician, a patient, and so forth may use endpoint device 160 to access AS 114 and/or AS 144. In one example, endpoint device 160 is connected directly to local area network 140. However, in another example, endpoint device may be a remote device that connects to local area network 140 and AS 144 via one or more of access network 120, access network 130 and or core network 110.

In one example, one or more of wearable devices, e.g., smart insoles 150C and EEG headset 152C, may also communicate with a cellular base station 121A and/or 121B of access network 120 to upload gait information and EEG information to a server performing functions for determining a medical condition regression. For example, the smart insoles 150C and EEG headset 152C may include a subscriber identity module (SIM) card, a cellular antenna and/or any other components that may be required to enable cellular communications via access network 120. Alternatively, or in addition, the smart insoles 150C and EEG headset 152C may communicate with access network 120 via cellular device 151. For example, cellular device 151 may comprise an intermediary unit, such as a cell phone, a personal base station, a femtocell or the like, for providing a tethering function to the smart insoles 150C and EEG headset 152C. In other words, the smart insoles 150C and EEG headset 152C and the cellular device 151 may communicate using various cellular communication standards or using near field communication techniques such as Wi-Fi/ IEEE 802.11, Bluetooth, ZigBee and so forth. Regardless of the specific technology or communication techniques used, access network 120 may thus receive gait information and EEG information from the smart insoles 150C and EEG headset 152C and forward such information to a server performing functions for determining a medical condition regression of the present disclosure.

In one example, the gait information and EEG information is uploaded to AS 114 in the core network 110. However, in another example, the gait information and EEG information may be passed to AS 144 in the local area network 140. For example, in one example gait information and EEG information of a user may still be managed via AS 144 in the local area network 140 when the user is not currently proximate to the local area network 140 and/or is not within range to communicate directly with components of local network 140.

In one example, local area network 140 may comprise an indoor network, e.g., a combination of wired and wireless LANs within a user's home or of a medical facility such as a hospital, a rehabilitation center, an elder care facility, and the like. Thus, local area network 140 and access network 120 may be complimentary to one another, with local area network 140 providing the capability of uploading gait information and EEG information while a user is indoors, and with the access network 120, e.g., a cellular network, providing coverage while the user is outdoors and/or while the user is outside of the communication range of the local area network 140.

In one example, each of the wearable devices 150A-150O and 152A-152C may be configured to connect to local area network 140 and the ZigBee access points 141A-141E when available, and to connect to access network 120 only when local area network 140 is not available. In one example, when connecting to access network 120, the cellular device 151 may time stamp gait information and EEG information as well as append to or include location information with the gait information and EEG information that it receives and uploads to a network-based server, e.g., AS 114. For example, if the gait information and EEG information is passed from the smart insoles 150C and EEG headset 152C via a cellular phone to access network 120, the cellular phone may reveal the GPS location information of the phone. Thus, the GPS location information of the phone can be associated with the contemporaneous gait information and EEG information of the smart insoles 150C and EEG headset 152C. As an alternative, or in addition, each of the base stations 121A and 121B may calculate location information of the device from which it receives the gait information or EEG information based upon cell tower triangulation, distance and direction estimation and so forth. Thus, when AS 114 and/or AS 114 receives gait information or EEG information, regardless of whether it is received from local area network 140 or from access network 120, it may include location information and/or time information, in addition to the other parameters such as acceleration, pressure, and so forth obtained by the sensors of one or more wearable devices.

It should be noted that the network 100 has been simplified. For example, the network 100 may include other network elements (not shown) such as border elements, routers, switches, policy servers, security devices, gateways, administrator and user consoles, and so forth.

Figure 2:
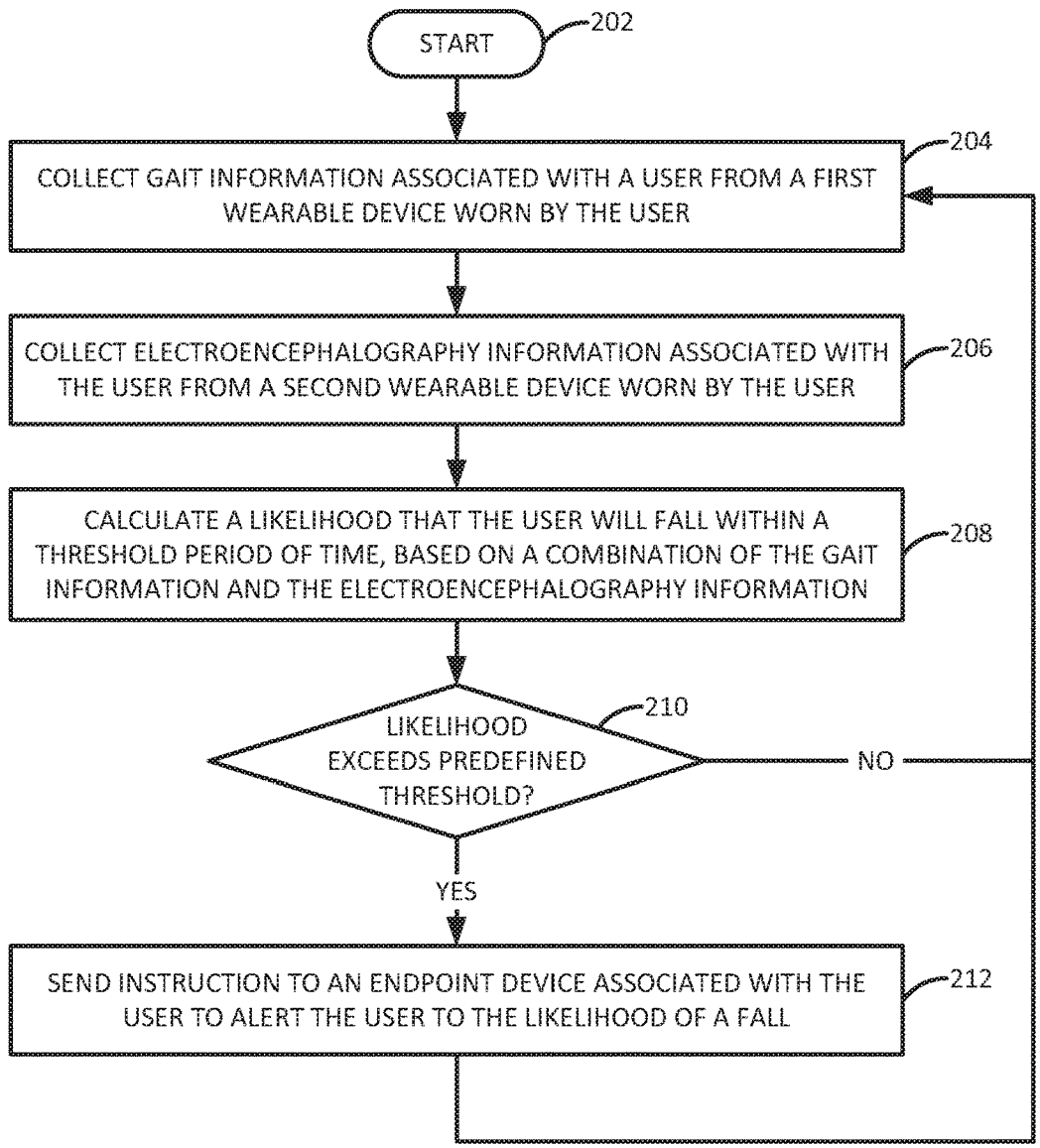
FIG. 2 illustrates an example flowchart of one example of a method for predicting a fall, according to the present disclosure.

FIG. 2 illustrates an example flowchart of one example of a method 200 for predicting a fall, according to the present disclosure. In one example, the method 200 may be performed by an application server such as AS 114 or AS 144 illustrated in FIG. 1. In one example, the steps, functions, or operations of method 200 may be performed by a computing device or system 300, and/or processor 302 as described in connection with FIG. 3 below. For illustrative purpose, the method 200 is described in greater detail below in connection with an example performed by a processor, such as processor 302.

The method 200 begins at step 202 and proceeds to step 204. In step 204, the processor may collect gait information associated with a user from a first wearable device worn by the user, such as smart insoles located in the user's shoes. As discussed above, a user's shoes may be outfitted with smart insoles that include force resisting sensors and/or other types of sensors. The sensors may measure and transmit raw gait information including pressure information, acceleration information, gyroscopic information, elevation information, temperature, time, and/or fluid content (edema) to the processor in real time (e.g., subject to any network conditions that may slow transmission time, such as latency). For instance, the sensors may stream the raw gait information to the processor. The gait information may include time stamps inserted by the smart insoles, by a cellular device communicatively coupled to the smart insoles (which may serve as a relay), or by a network access point via which the gait information may be transmitted.

In step 206, the processor may collect EEG information associated with the user from a second wearable device worn by the user, such as a mobile EEG headset worn on the user's head. As discussed above, a mobile EEG headset may include a plurality of electrodes or EEG sensors that may measure and transmit raw EEG information including patterns of brain electrical activity, acceleration information (including both linear and rotational accelerations), gyroscopic information, elevation information, time information, and/or location information. The EEG information may include time stamps inserted by the mobile EEG headset, by a cellular device communicatively coupled to the mobile EEG headset (which may serve as a relay), or by a network access point via which the EEG information may be transmitted.

In step 208, the processor may calculate a likelihood that the user is about to fall (e.g., within some predefined threshold period of time from the current time, such as within the next x seconds) based on a combination of the gait information collected in step 204 and the EEG information collected in step 206. In one example, the likelihood may be calculated by first quantifying one or more characteristics of the user's motion and/or neurological activity, based on the gait information and the EEG information. In a further example, the likelihood may also be based on one or more physical characteristics of the user, such as the user's height, weight, body mass index (BMI), age, known medical condition(s), and the like.

For instance, as discussed above, the gait information may allow for the calculation of a user's stride length, speed, acceleration, elevation, and/or mode of motion, while the EEG information may allow for the calculation of the user's reactions to a stimuli, neural oscillations, and/or eye blinks. Any of these characteristics may be compared to baseline characteristics, where the baseline characteristics may comprise ranges that are considered "safe." In other words, the more closely the user's motion or neurological activity characteristics match the baseline characteristics, the less likely the user is to fall. In one example, the baseline characteristics may comprise average values over a population of users. However, in other examples, the baseline characteristics may be computed for each user individually to better account for the users' individual physical conditions and abilities. Moreover, different baseline characteristics may be computed for different modes of motion and/or different known health conditions. For instance, the baseline stride length for running would be expected to be longer than the baseline stride length for walking. Similarly, the baseline neural oscillations for Alzheimer's disease would be expected to be different from the baseline neural oscillations for multiple sclerosis.

In one example, the likelihood that the user will fall is therefore quantified based on at least a first difference (i.e., reflecting the difference between a motion characteristic of the user and a baseline for the motion characteristic) and a second difference (i.e., reflecting the difference between a neurological activity characteristic of the user and a baseline for the neurological activity characteristic). In one example, the likelihood, F, that a user, u, is about to fall may be calculated as:

$$(|L_b - L_u|) * (|S_b - S_u|) * (|A_b - A_u|) * (|O_b - O_u|) \quad \text{(EQN. 1)}$$

where $L_b$ represents a baseline stride length, $L_u$ represents the user's stride length, $S_b$ represents a baseline speed for the mode of motion, $S_u$ represents the user's speed, $A_b$ represents a baseline acceleration for the mode of motion, $A_u$ represents the user's acceleration, $O_b$ represents a baseline neural oscillation (possibly for a specific health condition), and $O_u$ represents the user's neural oscillation. It should be noted that EQN. 1 could be extended to omit some of the motion and/or neurological activity characteristics shown and/or extended to include additional motion and/or neurological activity characteristics. Moreover, the individual differences could be weighted with different weights to give greater importance to characteristics that may be more indicative of a potential fall for a particular user, health condition, and/or mode of motion.

Referring back to FIG. 2, in step 210, the processor may determine whether the likelihood calculated in step 208 exceeds a predefined threshold. The predefined threshold may vary based on the particular user, mode of motion, and/or user's known health conditions (if any). If the processor concludes in step 210 that the likelihood does not exceed the predefined threshold, then the method 200 may return to step 204 and continue as discussed above, e.g., to collect further gait and EEG information. If, however, the processor concludes in step 210 that the likelihood does exceed the predefined threshold, then the method 200 may proceed to step 212.

In step 212, the processor may send an instruction to an endpoint device to alert the user (or the user's caregiver) to the fact that the user is likely to fall. The endpoint device may be, for example, the smart insoles, the mobile EEG headset, a mobile phone or other mobile device associated with the user (or the user's caregiver), or the like. The alert may take the form of an audible alert (e.g., a beep or tone), a visible alert (e.g., a flashing light), a haptic alert (a slight vibration), or another form. The alert may encourage the user (or the user's caregiver) to exercise increased caution (e.g., walk more slowly or take a break), to seek or offer physical assistance, or the like.

The method 200 may then return to step 204 and continue as discussed above, e.g., to collect further gait and EEG information. The monitoring may continue until the wearable devices are removed, powered down, run out of battery life, or the like.

It should be noted that the method 200 may be expanded to include additional steps. It should also be noted that although not specifically specified, one or more steps, functions or operations of the method 200 may include a storing, displaying and/or outputting step as required for a particular application. In other words, any data, records, fields, and/or intermediate results discussed in the respective methods can be stored, displayed and/or outputted to another device as required for a particular application. Furthermore, steps or blocks in FIGS. 2 that recite a determining operation or involve a decision do not necessarily require that both branches of the determining operation be practiced. In other words, one of the branches of the determining operation can be deemed as an optional step. In addition, one or more steps, blocks, functions, or operations of the above described method 200 may comprise optional steps, or can be combined, separated, and/or performed in a different order from that described above, without departing from the example examples of the present disclosure. For instance, steps 204 and 206 may be performed simultaneously. In addition, steps 204 and 206 may continue to be performed even as steps 208-212 are performed.

FIG. 3 depicts a high-level block diagram of a computing device programmed, or configured to perform the functions described herein. As depicted in FIG. 3, the system 300 comprises one or more hardware processor elements 302 (e.g., a central processing unit (CPU), a microprocessor, or a multi-core processor), a memory 304 (e.g., random access memory (RAM) and/or read only memory (ROM)), a module 305 for predicting falls, and various input/output devices 306 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computing device may employ a plurality of processor elements. Furthermore, although only one computing device is shown in the figure, if the method 200 as discussed above is implemented in a distributed or parallel manner for a particular illustrative example, i.e., the steps of the above method 200, or the entire method 200 is implemented across multiple or parallel computing device, then the computing device of this figure is intended to represent each of those multiple computing devices.

Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable gate array (PGA) including a Field PGA, or a state machine deployed on a hardware device, a computing device or any other hardware equivalents, e.g., computer readable instructions pertaining to the method(s) discussed above can be used to configure a hardware processor to perform the steps, functions and/or operations of the above disclosed method 200. In one example, instructions and data for the present module or process 305 for predicting falls (e.g., a software program comprising computer-executable instructions) can be loaded into memory 304 and executed by hardware processor element 302 to implement the steps, functions or operations as discussed above in connection with the illustrative method 200. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method can be perceived as a programmed processor or a specialized processor. As such, the present module 305 for predicting falls (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various examples have been described above, it should be understood that they have been presented by way of example only, and not limitation. Thus, the breadth and scope of a preferred example should not be limited by any of the above-described exemplary examples, but should be defined only in accordance with the following claims and their equivalents.

What is claimed is:

1. A method, comprising:
collecting, by a processor deployed in a communications network, gait information associated with a user from a first wearable device worn by the user;
collecting, by the processor, electroencephalography information associated with the user from a second wearable device worn by the user;
calculating, by the processor, a likelihood that the user will fall within a threshold period of time from a current time, wherein the calculating is based on a combination of the gait information and the electroencephalography information, wherein the likelihood is calculated as $(|L_b-L_u|)*(|S_b-S_u|)*(|A_b-A_u|)*(|O_b-O_u|)$, where $L_b$ represents a baseline stride length, $L_u$ represents a stride length of the user, $S_b$ represents a baseline speed for a mode of motion indicated by the gait information, $S_u$ represents a speed of the user, $A_b$ represents a baseline acceleration for the mode of motion, $A_u$ represents an acceleration of the user, $O_b$ represents a baseline neural oscillation, and $O_u$ represents a neural oscillation of the user; and
sending, by the processor, an instruction to an endpoint device associated with the user when the likelihood exceeds a predefined threshold, wherein the instruction instructs the endpoint device to generate an alert alerting the user that a fall is likely.

2. The method of claim 1, wherein the first wearable device comprises an insole worn in a shoe of the user.

3. The method of claim 2, wherein the insole comprises a plurality of force resisting sensors.

4. The method of claim 1, wherein the second wearable device comprises an electroencephalography headset worn on a head of the user.

5. The method of claim 4, wherein the electroencephalography headset comprises a plurality of electrodes.

6. The method of claim 1, wherein at least one of the first wearable device and the second wearable device includes a notification means for generating the alert.

7. The method of claim 1, wherein the gait information comprises a raw measurement of at least one of: pressure information, acceleration information, gyroscopic information, elevation information, a time, a temperature, and a fluid content.

8. The method of claim 1, wherein the electroencephalography information comprises a raw measurement of at least one of: brain electrical activity, acceleration information, gyroscopic information, elevation information, a time, and a location.

9. The method of claim 1, wherein the calculating the likelihood further accounts for at least one physical characteristic of the user.

10. The method of claim 9, wherein the at least one physical characteristic comprises at least one of: a height of the user, a weight of the user, a body mass index of the user, an age of the user, and a known medical condition of the user.

11. The method of claim 1, wherein at least one selected from a group of: the baseline stride length, the baseline speed for the mode of motion, the baseline acceleration for the mode of motion, and the baseline neural oscillation is user-specific.

12. The method of claim 1, wherein the baseline neural oscillation is associated with a specific health condition.

13. The method of claim 1, wherein the predefined threshold is specific to the user.

14. The method of claim 1, wherein the predefined threshold is specific to the mode of motion.

15. The method of claim 1, wherein the predefined threshold is specific to a known health condition of the user.

16. The method of claim 1, wherein $(|L_b-L_u|)$, $(|S_b-S_u|)$, $(|A_b-A_u|)$, and $(|O_b-O_u|)$, are assigned different weights that are specific to the user.

17. The method of claim 1, wherein $(|L_b-L_u|)$, $(|S_b-S_u|)$, $(|A_b-A_u|)$, and $(|O_b-O_u|)$, are assigned different weights that are specific to the mode of motion.

18. The method of claim 1, wherein $(|L_b-L_u|)$, $(|S_b-S_u|)$, $(|A_b-A_u|)$, and $(|O_b-O_u|)$, are assigned different weights that are specific to a known health condition of the user.

19. A non-transitory computer-readable storage device storing instructions which, when executed by a processor deployed in a communication network, cause the processor to perform operations, the operations comprising:

collecting gait information associated with a user from a first wearable device worn by the user;

collecting electroencephalography information associated with the user from a second wearable device worn by the user;

calculating a likelihood that the user will fall within a threshold period of time from a current time, wherein the calculating is based on a combination of the gait information and the electroencephalography information, wherein the likelihood is calculated as $(|L_b-L_u|)*(|S_b-S_u|)*(|A_b-A_u|)*(|O_b-O_u|)$, where $L_b$ represents a baseline stride length, $L_u$ represents a stride length of the user, $S_b$ represents a baseline speed for a mode of motion indicated by the gait information, $S_u$ represents a speed of the user, $A_b$ represents a baseline acceleration for the mode of motion, $A_u$ represents an acceleration of the user, $O_b$ represents a baseline neural oscillation, and $O_u$ represents a neural oscillation of the user; and sending an instruction to an endpoint device associated with the user when the likelihood exceeds a predefined threshold, wherein the instruction instructs the endpoint device to generate an alert alerting the user that a fall is likely.

20. An apparatus, comprising:

a processor deployed in a communication network; and a non-transitory computer-readable medium storing instructions which, when executed by the processor, cause the processor to perform operations, the operations comprising:

collecting gait information associated with a user from a first wearable device worn by the user;

collecting electroencephalography information associated with the user from a second wearable device worn by the user;

calculating a likelihood that the user will fall within a threshold period of time from a current time, wherein the calculating is based on a combination of the gait information and the electroencephalography information, wherein the likelihood is calculated as $(|L_b-L_u|)*(|S_b-S_u|)*(|A_b-A_u|)*(|O_b-O_u|)$, where $L_b$ represents a baseline stride length, $L_u$ represents a stride length of the user, $S_b$ represents a baseline speed for a mode of motion indicated by the gait information, $S_u$ represents a speed of the user, $A_b$ represents a baseline acceleration for the mode of motion, $A_u$ represents an acceleration of the user, $O_b$ represents a baseline neural oscillation, and $O_u$ represents a neural oscillation of the user; and sending an instruction to an endpoint device associated with the user when the likelihood exceeds a predefined threshold, wherein the instruction instructs the endpoint device to generate an alert alerting the user that a fall is likely.

* * * * *